United States Patent [19]

Bodenschatz et al.

[11] Patent Number: 5,419,161
[45] Date of Patent: May 30, 1995

[54] ARTICULAR BANDAGE HAVING WAXY STRUCTURE INSERTS

[75] Inventors: Stefan Bodenschatz; Wolfgang Feldberger; Hans Spenke, all of Emmerich, Germany

[73] Assignee: Beiersdorf AG, Hamburg, Germany

[21] Appl. No.: 227,918

[22] Filed: Apr. 15, 1994

Related U.S. Application Data

[63] Continuation of Ser. No. 815,271, Dec. 27, 1991.

Foreign Application Priority Data

Dec. 27, 1991 [DE] Germany ............ 41 03 386.8

[51] Int. Cl.⁶ ............ D04B 1/22; D04B 1/18; D04B 7/10; A61F 13/00
[52] U.S. Cl. ............ 66/172 E; 66/169 R; 66/196; 2/16; 2/22; 602/60; 602/61; 602/76
[58] Field of Search ............ 2/16, 22; 66/169, 172 E, 66/172 R, 196; 602/62, 63, 75, 76, 60, 61, 64, 65, 66, 900

[56] References Cited

U.S. PATENT DOCUMENTS

| | | | |
|---|---|---|---|
| 663,749 | 12/1900 | Gorse | 602/60 |
| 2,485,725 | 10/1949 | Francis, Jr. | 602/75 X |
| 2,703,971 | 3/1955 | Bausher | 66/172 E |
| 3,322,118 | 5/1967 | Sotherlim | 2/16 X |
| 4,048,818 | 9/1977 | Cueman | 66/172 E |
| 4,269,181 | 5/1981 | Delannoy | 602/63 X |
| 4,476,858 | 10/1984 | Curtis | 602/62 X |
| 4,492,227 | 1/1985 | Senn et al. | 602/63 |
| 4,624,015 | 11/1986 | Bottoms | 2/22 |
| 4,630,455 | 12/1986 | Lingenfelter | 66/172 R |
| 4,674,489 | 6/1987 | Lundy | 602/76 |
| 4,702,091 | 10/1987 | Good et al. | 66/172 E X |
| 5,133,199 | 7/1992 | Parikh et al. | 602/76 X |
| 5,154,690 | 10/1992 | Shiono | 602/61 X |

*Primary Examiner*—John J. Calvert
*Attorney, Agent, or Firm*—Anderson Kill Olick & Oshinsky

[57] ABSTRACT

Described is a fabric produced from textile threads, more particularly a knitted fabric, for use within the flexion area of articulated bandages. The knitted fabric is incorporated into the articulated bandage (2) in the form of an insert (8). In order to eliminate the formation of creases within the flexion area of the articular bandage, a transverse wave structure is formed on at least one side, which, by the use of an elastic thread arrangement which is incorporated or located underneath a top structure, is elastically pretensioned and stabilized and is connected to the top structure at predetermined intervals or according to a specific rule.

9 Claims, 4 Drawing Sheets

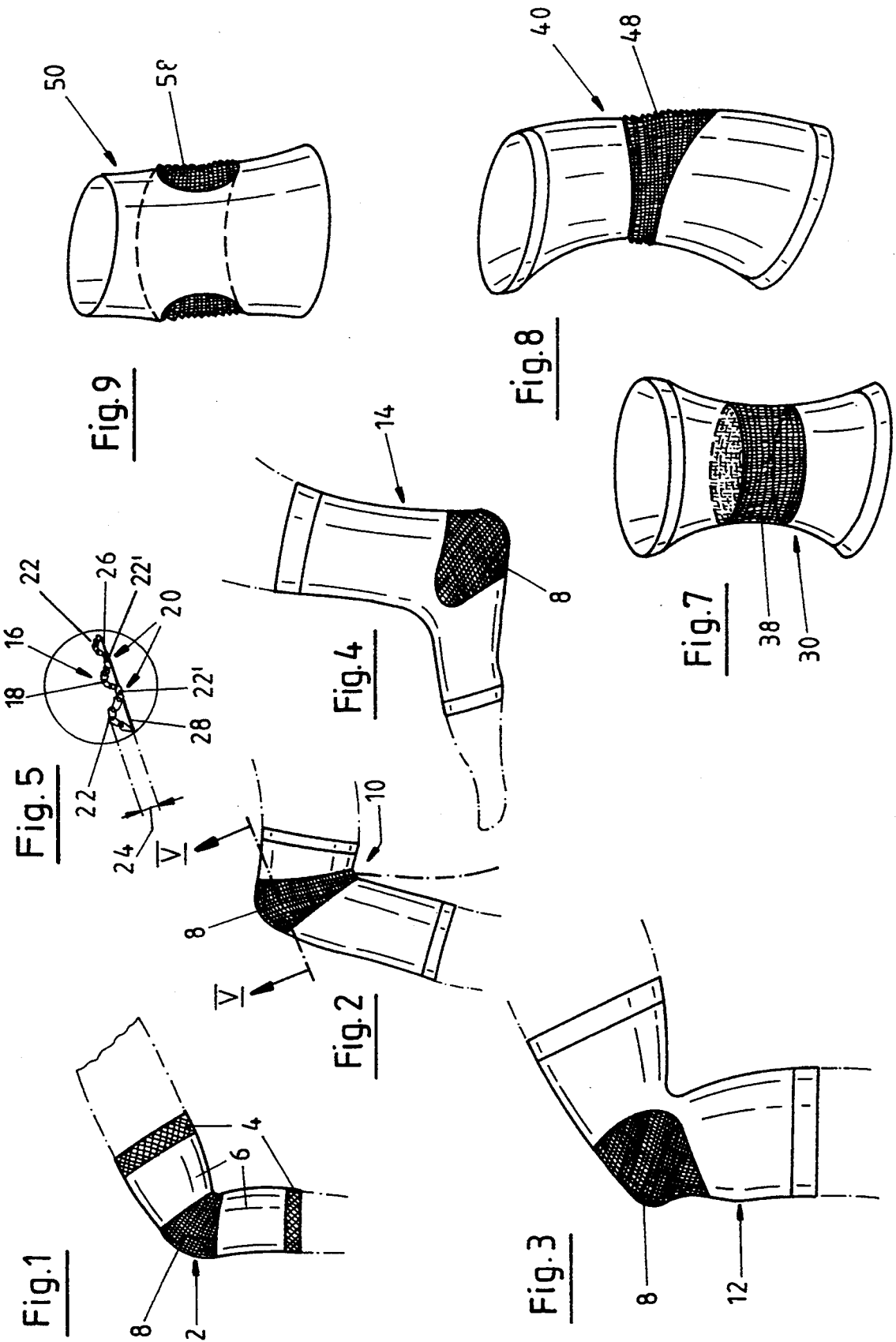

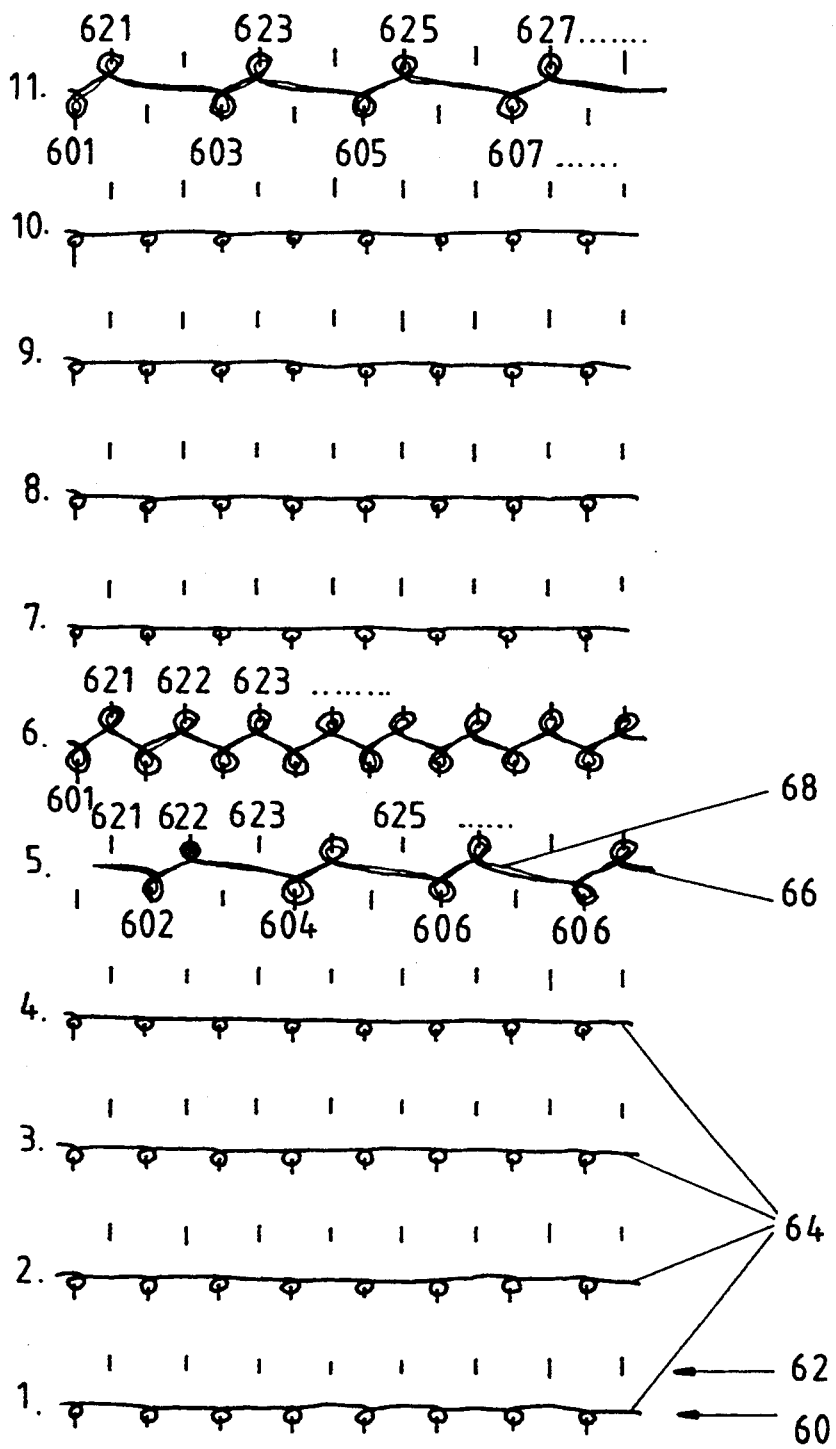

5,419,161

ARTICULAR BANDAGE HAVING WAVY STRUCTURE INSERTS

This is a continuation application of Ser. No. 07/815,271, filed Dec. 27, 1991.

FIELD OF THE INVENTION

The present invention relates to a fabric produced from textile threads, more particularly to a knitted fabric which can be used within the flexion area of articular bandages.

BACKGROUND OF THE INVENTION

Articular bandages are known in many forms and are employed for the most widely varying parts of the human and animal body in the case of articular traumata to support the joint by compression or by incorporating additional stabilizing members. Most frequently, such bandages are constructed in the form of bandages for the ankle, knee, wrist, elbow and shoulder joints.

For articular bandages, the problem of an undesirable formation of creases frequently occurs because of the relatively large flexural angle. It is possible to counteract this problem by the bandage, at least within the critical areas of flexion a more elastic yarn. However, such yarns are relatively expensive. Furthermore, in the extended or rest stage of the joint, excessive compression is produced which may lead to ligations of the blood vessels and accordingly creates problems when the bandage is worn.

An object of the invention is therefore to provide a fabric produced from textile threads for use within the inner and outer flexion area of articular bandages and which is economical to manufacture and will preclude creases within the area of flexion, even after prolonged use, and provide better comfort. Further technical problems arise when providing an articular bandage which is fitted with such a fabric produced from textile threads.

Another object of the invention is therefore to provide a simple method for the production of the fabric.

SUMMARY OF THE INVENTION

To achieve these and other aspects of the invention, which shall become apparent hereafter, a fabric produced from textile threads and an articular bandage fabricated therefrom comprised of textile threads is constructed in such a way that, at least on one side, relief in the form of a wavy structure is created. This wavy structure is elastically pretensioned and stabilized by a subjacent thread arrangement of more highly elastic yarn or thread, as a result of which the top structure, in the relaxed state of the fabric, bulges out in a wave-like, though preferably in a half wave-like manner. The fabric structure is used in articular bandages and is stressed vertically to the orientation of the transverse waves which is the case when the bandaged joint is flexed and the transverse waves are drawn to be flatter or smoother without an extension in length or any strain of the top structure taking place. In this way, it is possible to preclude an overstretching of the top structure and thereby avoid creases even after a prolonged use of the bandage. Thus, the fabric according to the invention is especially suitable for use in articular bandages, which are used for joints (e.g., elbow, knee or shoulder bandages) having greater freedom of movement or large flexural angles.

The textile fabric of the invention, in spite of a relatively high elongation capacity, thus permits the use of relatively inelastic yarn for the top structure and facilitates economical production of the textile fabric.

The fabric produced from textile threads possessing the properties described above can be formed particularly advantageously in the form of a knitted fabric since a high basic elasticity of the textile fabric is already provided. It is additionally possible to reduce the risk of excessive stretching of the yarn with this design.

The textile fabric according to the invention is preferably used in an articular bandage only within areas, viz. where the greatest elongation paths are to be expected. The orientation of the transverse waves takes place regularly vertically to the main direction of elongation. It is also possible to have several textile fabric structures in which the respective transverse wave orientations are at an angle to each other within the area of the artificial bandage most highly stressed by the flexion of the joint. This arrangement is made in harmonization with the respective special function of the articular bandage.

The elastic thread arrangement is knitted concurrently with the knitted top fabric in same operation which results in an advantageous production method. This method is especially suitable for the automation of the manufacturing methods in which a minimum of yarn possessing and increased elasticity is required.

It has been shown that when the knitted top fabric is comprised or ordinary yarn, such as cotton and/or polyamide yarn, a sufficiently high elasticity of the knitted fabric is already provided to prevent creases during the service life of the bandage. It is also possible, however, to incorporate into the top fabric a laid-in thread in order to produce an additional compression effect also within this area.

If the yarn of the elastic thread arrangement is plaited, a significantly improved war resistance results, especially within the flexion area of the articular bandage, has a positive effect since relative movements between bandage and skin occur there to an increased extent.

BRIEF DESCRIPTION OF THE DRAWINGS

The invention will be better understood by the Detailed Description of the Preferred Embodiments, with reference to the drawings of which:

FIGS. 1 through 4 show various configurations of the textile fabric according to the invention in different articular bandages;

FIG. 5 shows a detail of the section V—V in FIG. 2;

FIGS. 7 through 9 show further embodiments of articular bandages;

FIG. 10 shows representations of knitting courses in order to illustrate a first embodiment of the method for the production of a knitted fabric according to the invention.

DETAILED DESCRIPTION OF THE PREFERRED AND ALTERNATE EMBODIMENTS

Figure 6:
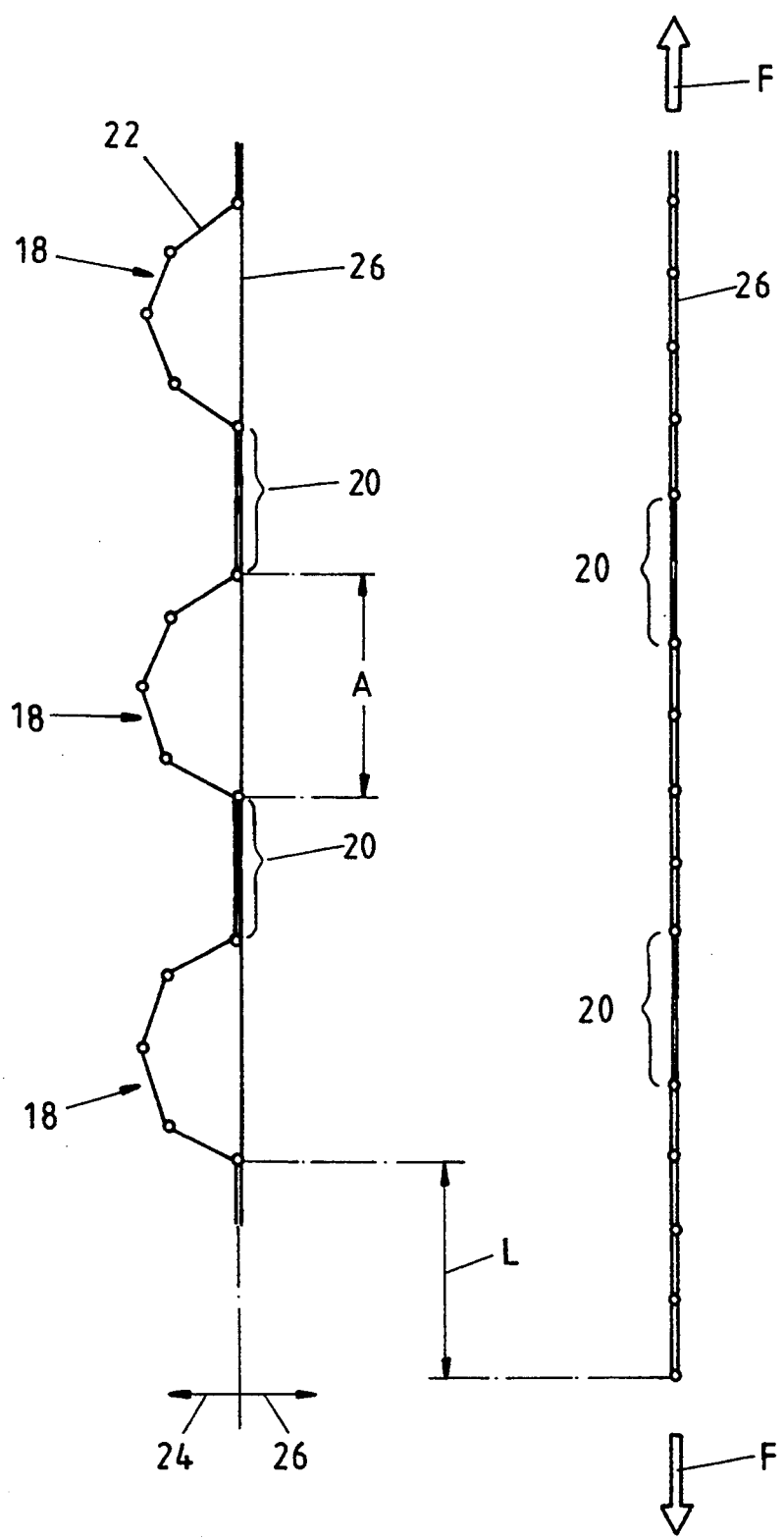
FIG. 6 shows, in a diagrammatically simplified representation, the principle of the deformation of the fabric produced from textile threads.

In FIG. 1, the articular part within the area of an elbow is drawn which is stabilized by an elbow joint bandage 2. This is an elastic bandage in tubular form, a so-called compressive bandage, used for cases of articular traumata or articular weaknesses. Substantially, the bandage comprises three sections. On the edge side, a top section 4 is provided to insure slip-resistance of the bandage 2. This is followed by an actual compression section 6, which passes over the joint. In the compression section 76, an insert 8 is incorporated at the point where the greatest elongation of the bandage 2 takes place.

In FIGS. 2 through 4, further articular bandages, viz. a shoulder bandage 10 (FIG. 2), a knee joint bandage (FIG. 3) and a ankle joint bandage 14 (FIG. 4) are depicted. These bandages are constructed similarly to the elbow joint bandage 2 and are provided with inserts 8 in the compression section. These inserts are identified by longitudinal striations in the figures.

Bandages 2 and 10 through 14 include different knitting constructions for the individual sections 4, 6 and 8. However, it is also possible to make use of other textile constructions and/or knitted fabrics.

A feature of the bandages shown is that, for the inserts 8 which are provided at the point where the greatest alternating stresses of the bandage occur, a special textile structure, more particularly a special knitted fabric, is used, which will be explained in greater detail below.

The strip-like floating of the inserts 8 indicates that, within this area, the knitted fabric forms a relief which is explained by the section line V—V in FIG. 2 and which is identified with the reference number 16. In this relief, a wavy structure is involved, which is formed at least one the one side of the bandage—in the embodiment shown on the side facing away from the body—In this case, a series of half waves 18 are lined up next to each other with the interposition of connected points or connecting zones 20 which are produced as detailed below.

A top knitted fabric 24 formed by stiches 22 is, with an elastic thread arrangement 26, rigidly connected to the underside of the knitted top cover 24 in such a way that a row of stiches 22 of the top knitted fabric—four in the embodiment—are bridged by a layer stich 28 of the elastic thread arrangement 26 located therebeneath. The stiches 22 between the connected points or zones 20 are made to bulge upwardly due to the elastic thread arrangement as a result of which the transverse waves 18 are pretensioned and stabilized.

By varying the number of the bridged stiches 22 and/or the layer stiches 28, it is possible to influence the deformational behavior and the permanent elasticity. The deformational behavior of the knitted fabric formed in this manner becomes apparent from the representation in FIG. 6. On the left-hand side, the knitted fabric is shown in a relaxed state. The stiches are indicated with lines and the interconnection of the stiches with small circles.

The elastic yarn provided on the underside bridges the connecting zones 20, between which, in each case, four stiches 22 of the top knitted fabric are constructed. By pretensioning of the elastic thread arrangement, the stiches 22 are made to bulge out to form half waves 18, producing the relief structure. The half waves 18 possess in each case between two and twelve, although preferably four stich courses.

The right-hand side depicts how the knitted fabric behaves when it is subjected to the stress of a tensile force F. It can be seen that the elastic thread arrangement between the connecting zones 20 is elongated without additional stress taking place within the area of the half waves 18, i.e., within the area of the stiches 22. Accordingly, the knitted fabric is capable of being elongated by the dimension L before the stiches 22 of the top knitted fabric are subjected to tensile stress. Accordingly, this dimension L provides an elongation reserve of the knitted bandage fabric, as compared to conventional textile fabrics.

The connection between top knitted fabric and elastic thread arrangement may be established in the most widely varied ways. It is possible also to select or establish the connection so that waves are formed on both sides of the knitted fabric. Nor is the invention restricted to the top knitted fabric being constructed as a single face fabric.

By the above structure of the knitted fabric, in spite of the provision of a high elongation elasticity for the knitted top fabric, it is possible to use normal knitting yarn such as cotton or polyamide yarn. For the elastic thread arrangement 26, preferably higher-elastic yarn, such as covered yarn, is used. In this case, it is possible for this elastic thread to be additionally plaited to improve the resistance to wear of the fabric.

It is furthermore possible to incorporate a laid-in thread into the stiches 22 of the top knitted fabric to achieve a compression effect of the bandage, also within this area of the wavy relief structure.

The wavy knitted fabric produced in this manner can be inserted into the bandage at the most widely varied points and in the most widely varied configurations, which is intended as shown in FIGS. 7 through 9. The wavy knitted fabric may also be topstitched with, for instance, elastic yarn.

In the tubular articular bandage 30 depicted in FIG. 7, the elastic insert 38 extends over the entire circumference at a regular level. In the bandage 40 of FIG. 8, the insert 48 also extends in an annular manner around the tubular bandage, but has, on one side, a greater extension than on the other.

Finally, the bandage 50 of FIG. 9 has an insert 58 which extends with a substantially uniform width over a sector angle of approximately 180° around the bandage.

While departing from the disclosed embodiments, it is also possible to operate within the area of flexion of the articular bandages with several differently oriented inserts in order to allow, in this manner, for the specific stress the bandage is subjected to.

Figure 11:
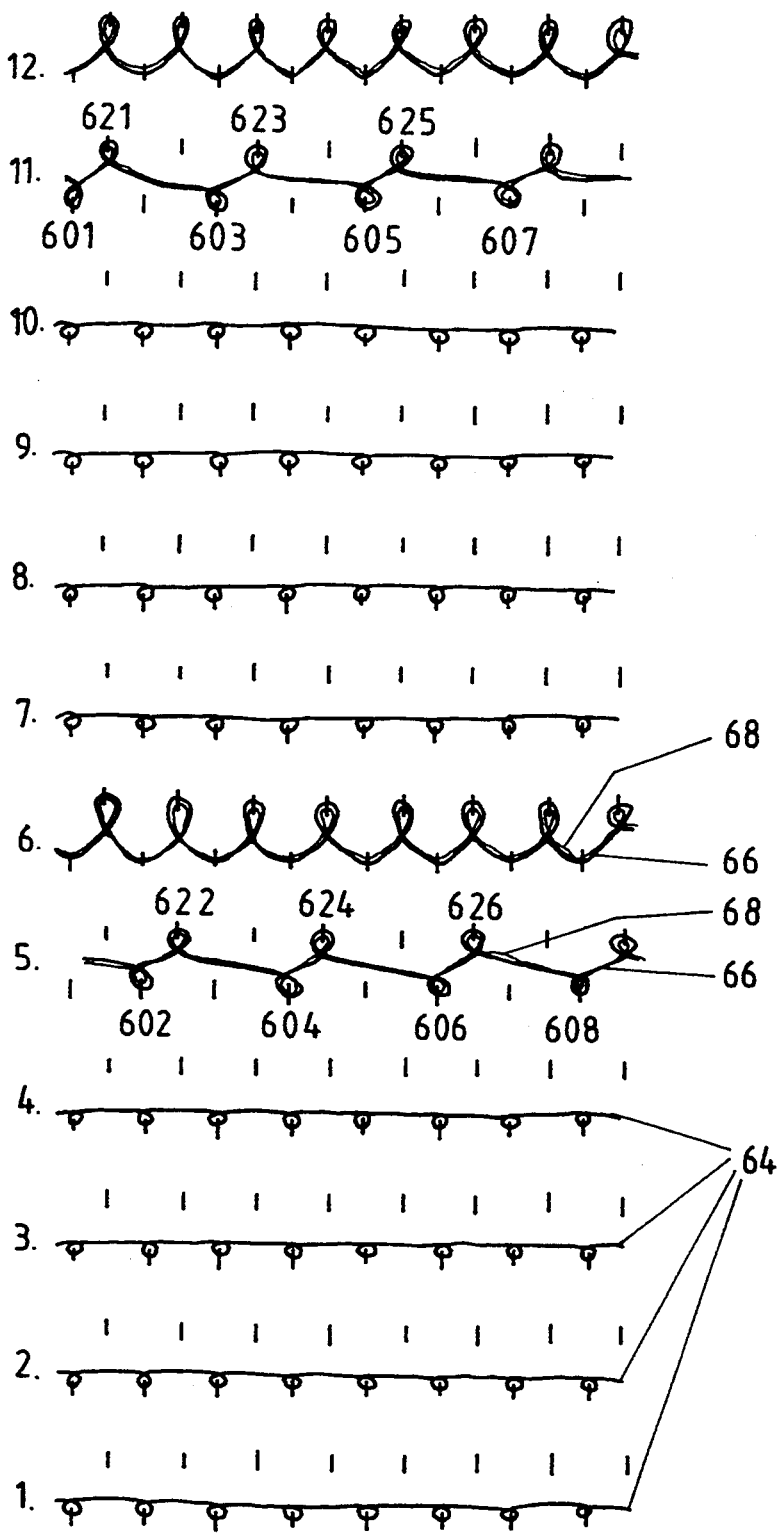
FIG. 11 shows, in a representation similar to the FIG. 10, a further knitting pattern for the knitted fabric.

In the FIGS. 10 and 11, two possibilities are shown how the wavy knitted fabric described in the foregoing can be manufactured on automatic knitting machines, viz. a first needle bed 60 and a second needle bed 62 with needles disposed at regular intervals from each other. On the first needle bed 60, several—four in the embodiment shown—rows of stiches of normal knitting yarn such as cotton or polyamide yarn 64 are knitted. Subsequently two rows of stiches are knitted on both needle beds 60, 62 with elastic yarn, such as rubber or cover yearn 68, in which connection a plaiting thread 66 is preferably added to this elastic yarn. In the fifth knitting course, knitting is carried out only on selected needles 602, 604, 606, . . . etc., and 622, 624, 626, . . . etc., of both needle beds. The plaiting thread may be formed of a polyamide high-elasticity thread. The illustration reveals that the stich course 6 is again knitted on all the needles of the two needle beds 60, 62.

Then four courses of stiches with ordinary yarn follow again on the first needle bed 60 and, in conclusion, two further courses of stiches with an elastic yarn, in which case the eleventh knitting course differs from the fifth in that the participating needles of the needle beds 60, 62 are staggered by one.

FIG. 11 shows another pattern with a somewhat different knitting construction within the area of the knitting fabric connections 20. The knitting courses one through five and seven through eleven correspond to the knitting pattern of FIG. 10. What differs is the construction of the knitting courses 6 or 12, so that it does not appear necessary to discuss this Figure in greater detail.

Deviating from the previously described manufacturing method, it is also possible to knit on a needle bed one or several courses of stiches from elastic yarn such as cover yarn and, on the other needle bed, rows of stiches from normal knitting yarn. In this case, one or more courses of stiches are subsequently knitted with all or with individual needles of both needle beds.

The invention is not restricted to the fabric produced from textile threads to be constructed in the form of a knitted fabric. The textile fabric receives such a construction that an either incorporated or an elastic thread arrangement connected with a textile top structure according to a predetermined pattern imparts to the fabric such an internal pretension that, at least on one side, a wave-like relief is produced which, by means of external stress, can then be drawn smooth or smoother without the top structure being subjected to elongation stress at this stage.

The invention thus provides a fabric produced from textile threads, more particularly a knitted fabric, for use within the area of flexion of articular bandages. In order to eliminate the formation of creases within the flexion area of the articular bandage, a transverse wavy structure is formed at least on one side which, by means of the thread arrangement which is either incorporated or located underneath a top structure, which, a predetermined intervals or according to a specific rule, is connected to the top structure, is elastically pretensioned and stabilized.

While the preferred and alternate embodiments of the invention have been described in detail, it must be understood that modifications and adaptations may be made thereto, without departing from the spirit and scope of the invention as delineated in the following claims:

What is claimed is:

1. A tubular articulate structure having a top section and a bottom section for holding the bandage in place and a middle section forming a compression area, said structure comprising:
   an insert made of a fabric manufactured from textile threads, such that said insert is placeable over and adjacent to a bending area of a joint of a user, the insert being integral with the compression area and having fabric that is a wavy structure in the form of transversal waves;
   wherein the transversal waves are oriented essentially perpendicularly to a horizontal stretch direction, wherein the wavy structure formed by multiple stitches, is elastically pretensioned and stabilized by means of an elastic thread arrangement having fewer stitches than the wavy structure incorporated into a stitch course-like manner and connected at predetermined intervals to the elastic thread arrangement in at least one zone of a covering structure; and
   wherein the greatest number of transversal waves is located where the greatest horizontal elongation occurs due to the bending of the joint and the elongation of the fabric in the compression area.

2. The tubular articulate structure according to claim 1, wherein the transversal waves each containing from 2 to 12 stitch courses.

3. The tubular articulate structure according to claim 1, wherein the outer layer or covering fabric of the wavy structure is manufactured from inelastic threads.

4. The tubular articulate structure according to claim 1, wherein the covering fabric (24) is comprised of cotton, polyamide yarn or a combination thereof.

5. The tubular articulate structure according to claim 1, wherein the elastic thread arrangement is comprised of covered yarn.

6. The tubular articulate structure according to claim 5, wherein the covered yarn is plaited.

7. The tubular articulate structure according to claim 1, wherein a laid-in thread is incorporated into the covering fabric (24).

8. The tubular articulate structure according to claim 1, wherein the joint bandage (2) possesses an annular insert of the fabric providing a greater extension than in the compression area.

9. The tubular articulate structure according to claim 1, wherein the joint bandage is provided with an insert of a fabric (58) that extends with a uniform width across a centering angle of approximately 180 around the joint bandage (2) comprise at least two to twelve stitch courses.

* * * * *